United States Patent [19]

Novack et al.

[11] Patent Number: 4,916,935
[45] Date of Patent: Apr. 17, 1990

[54] LOW POWER SOLID STATE GAS SENSOR WITH LINEAR OUTPUT AND METHOD OF MAKING THE SAME

[75] Inventors: Robert L. Novack, Evans City; John E. Tozier, Wexford, both of Pa.

[73] Assignee: Bacharach, Inc., Pittsburgh, Pa.

[21] Appl. No.: 299,690

[22] Filed: Jan. 23, 1989

Related U.S. Application Data

[63] Continuation-in-part of Ser. No. 550,280, Nov. 9, 1983.

[51] Int. Cl.[4] ............................................. G01N 27/12
[52] U.S. Cl. ...................................... 73/27 R; 338/34; 422/98
[58] Field of Search ........................... 73/23, 26, 27 R; 422/95, 98; 324/71.5; 340/634; 338/34

[56] References Cited

U.S. PATENT DOCUMENTS

| | | | |
|---|---|---|---|
| 3,440,017 | 1/1969 | Palmer | 23/254 |
| 3,631,436 | 7/1970 | Taguchi | 340/237 |
| 3,732,519 | 5/1973 | Taguchi | 338/34 |
| 3,751,968 | 8/1973 | Loh et al. | 73/23 |
| 3,835,529 | 9/1974 | Taguchi | 29/570 |
| 3,865,550 | 2/1975 | Bott et al. | 23/232 |
| 3,886,785 | 6/1975 | Stadler et al. | 73/23 |
| 3,955,268 | 5/1976 | Chou et al. | 29/570 |
| 3,959,764 | 5/1976 | Allman | 338/34 |
| 3,979,625 | 9/1976 | Roberts | 313/230 |
| 4,004,452 | 1/1977 | Logothetis et al. | 73/23 |
| 4,013,943 | 3/1977 | Chou et al. | 324/33 |
| 4,112,356 | 9/1978 | Toy | 324/71 |
| 4,203,726 | 5/1980 | Patterson | 23/232 |
| 4,308,518 | 12/1981 | Hattori et al. | 338/34 |
| 4,338,281 | 7/1982 | Treitinger et al. | 422/98 |
| 4,447,397 | 5/1984 | Anouchi et al. | 422/94 |

FOREIGN PATENT DOCUMENTS

| | | | |
|---|---|---|---|
| 94152 | 7/1980 | Japan | 422/95 |
| 49950 | 5/1981 | Japan | 338/34 |
| 132555 | 10/1981 | Japan | 338/34 |

Primary Examiner—Hezron E. Williams
Attorney, Agent, or Firm—Webb, Burden, Ziesenheim & Webb

[57] ABSTRACT

The present invention is directed towards a low power, solid state gas sensor and method of making the same. The sensor comprises a heating element formed from a wire coiled about an axis, a sensing whisker placed inside the heating coil substantially in plane with said axis, and a metal oxide semiconductor material whose resistance varies with the object gas concentration. The gas sensors of this type operate at less than 150 mA. In addition, gas sensors of the present invention exhibit a substantially linear response over a significant concentration of the object gas.

8 Claims, 2 Drawing Sheets

LOW POWER SOLID STATE GAS SENSOR WITH LINEAR OUTPUT AND METHOD OF MAKING THE SAME

RELATED APPLICATIONS

This application is a continuation-in-part of application Ser. No. 550,280, filed Nov. 9, 1983.

TECHNICAL FIELD

The field of art to which this invention pertains is detection of gaseous impurities in air, more particularly to gas sensors employing metal oxide semiconductors in the construction of said sensors.

BACKGROUND ART

Metal oxide semiconductor gas sensors are well known and have been used for many years. These sensors apply the principle that when a metal oxide semiconductor is exposed to a particular reactive gas, its electrical resistance changes as a function of the concentration of the reactive gas.

Typically, these gas sensors have been used to detect, among other things, oxygen in fuel exhaust systems to determine the fuel to air ratios for improved efficiency in combustion engines, as well as determining dangerous concentrations of poisonous gases in mine shafts, welding operations, and other areas where certain gases such as methane, $H_2S$ and CO can present potential dangers. There have been a number of gas sensors which have been developed over the years utilizing a variety of materials and designs. These designs generally consist of a semiconductor material, electrical leads, a power source, and a heating device of some sort. These sensor designs to date have been relatively complex. Certain designs require that the semiconductor be comprised of a conducting and nonconducting metal oxide mixture as in U.S. Pat. Nos. 3,865,550; 3,955,268 and 4,013,943. Other designs have required that the metal oxide semiconductor material be supported on a substrate of some sort, U.S. Pat. No. 4,338,281. And still others have configurations which require temperatures in excess of 700° C or have current requirements greater than 150 mA, U.S. Pat. Nos. 3,886,785; 4,004,452 and 3,955,268. Many of these gas sensors have found their greatest utility in portable gas detecting units. However, the prior art sensing units have a number of drawbacks when applied in these units. Primarily, it is the fact that they require a significant amount of power to operate which does not make them efficient in battery powered devices. Their high power consumption is due in general to a number of reasons, one reason being the high temperatures at which these sensors operate requiring greater current flow through the heater. Another is the poor design which results in bulky, high mass sensors or which require more power to heat them to their operating temperatures. In many instances, this is due to the inefficient design which ultimately leads to a larger than necessary mass for the sensor requiring more energy to maintain their operating temperature. Since these sensors must be maintained at a relatively high temperature, the greater the mass, the more current must be used to heat them. This increase in power drain makes these sensors less desirable for use in small portable units.

Therefore, what is needed in the art is a low power consuming, metal oxide semiconductor gas sensor, whose power requirements are significantly lower than the present gas sensors. Such a sensor would make a truly portable gas sensing system practical.

DISCLOSURE OF INVENTION

The present invention encompasses a novel porous metal oxide semiconductor solid state gas sensor. The sensor incorporates a heating element in the shape of a number of coils wound around a central axis, a sensing whisker substantially in a plane parallel to this axis passing through the coils, a metal oxide semiconductor material whose electrical conductivity or resistivity is altered by contact with a specific object gas, encapsulating both the heating element and the sensor. This design allows for the construction of a mechanically stable gas sensor having self-heating capability and requiring less than 150 mA of current during operation and is capable of responding in a linear fashion over a significant concentration of an object gas.

Another aspect of the present invention is a method of detecting an object gas utilizing the present inventive sensor and a method of making the sensor.

Other features and advantages will be apparent from the specification and claims and from the accompanying drawings which illustrate an embodiment of the invention.

BEST MODE FOR CARRYING OUT THE INVENTION

Figure 1:
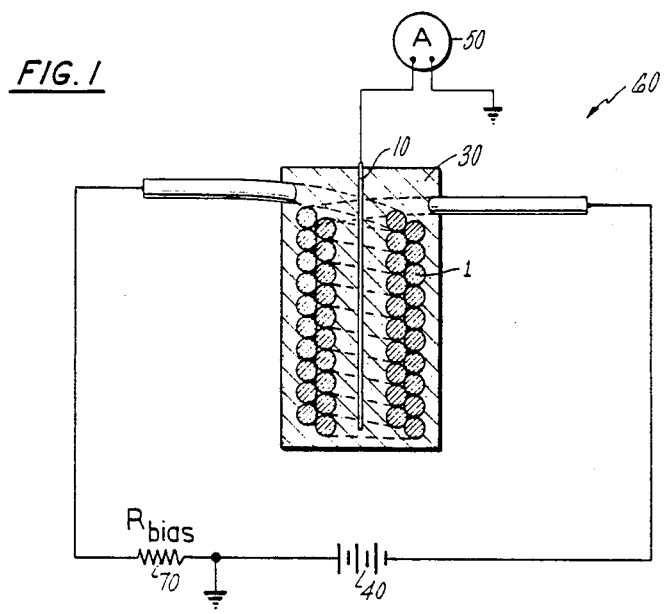
FIG. 1 depicts a gas sensor of the present design.

As shown in FIG. 1, the solid state gas sensor is comprised of a coiled heater 1, a sensing whisker 10 and a porous metal oxide semiconductor material 30.

The wire which forms the heater coil 1 may be any electrically resistive wire. Preferably the wire is of a noble metal or a noble metal alloy, i.e. those of the $P_t$ Group, (Rh, Ir, Pd, etc.) and has sufficient temperature stability at the operating temperatures of the detector. One particularly desirable wire is one comprised of about 10% iridium and about 90% platinum. In general, the wire should have a diameter of about 1 mil or less, be insulated with a porous insulating material such as aluminum oxide, and be flexible to allow it to be formed into a coil shape. One purpose of the insulation is to allow close stacking or contacting of the coils, but prevent the conductor in the coils from contacting each other and electrically shorting out. It is necessary that the insulation be porous and allow the semiconductor metal oxide to contact the wire and provide a pathway for the current to flow directly to the whisker.

The wire used to form the coiled heater is preferably coated with an insulating pigment bound to the wire with a high temperature silicone resinous material. The coating should be flexible to permit sharp radius bending of the wire, such as during coiling, without loss of the insulating pigment. In addition, the insulating pigment should remain in place after the coiled wire is heated to red heat during a subsequent curing process. Enough of the resinous material remains to bind the pigment to the wire and keep its desirable insulatory ability. However, a sufficient amount of the resinous material burns away during curing to make the coating porous and open up the conductive wire to contact with the semiconductor metal oxide.

Desirable insulating pigments include alumina ($Al_2O_3$), magnesium oxide, and other insulating oxide particles, although alumina is preferred. Binders for the insulating particles must be flexible in the uncured state and have sufficient adhesive properties after curing to hold the insulating particles in place. In addition, a sufficient portion of the binder must burn away to make the layer porous. Suitable binders include the silicone resins primarily, although others may be found to be suitable. A particularly known resin is Dow Corning ® 997 Varnish.

A suitable mil 90% platinum, 10% iridium alloy heater wire, coated with about a 1 mil layer of alumina particles in a silicone resin binder is sold by Secon Metals, 7 Intervale Street, White Plains, N.Y. as a ceramic coated filament wire with a type E ceramic coating. The ceramic coating is green or uncured when initially purchased. This wire has an outer diameter of about 0.0025 inch and a resistance of about 140 ohms per foot. This wire is also generally known as a ceramic coated filament wire.

It is believed that the carbon portion of the silicone resin binder burns away during the initial curing and glass ($SiO_2$) is left behind. Enough of the glass remains to hold the alumina particles in place and provide an insulative layer, yet the coating on the wire is porous enough to permit a metal oxide semiconductor material to flow therein and make electrical contact with the wire.

The heater coil 1 may be formed by spirally winding the wire about a mandrel or other suitable form to create a series of tightly wound continuous loops. Depending on the configuration of the sensor, its temperature requirements, as well as the diameter and the resistance of the wire, the heater coil may be formed by continuously winding a series of subsequent layers of coils overlaying the previously formed coils as depicted in FIG. 1. In general, each of the subsequent layers of coils should be formed such that the coils in the subsequent layer are out of alignment with the primary layer by about $\frac{1}{2}$ turn forming a more compact coil arrangement.

The sensing whisker which is to be positioned within the heater coil may be, but need not be, made of the same material as that used in the heater coil. The wire must be electrically conductive and should be equal to or less than about 1 mil in diameter. This sensing whisker can be insulated in a similar fashion to that of the coil, however, raw, uninsulated wire can also be used. The porous insulation on the whisker, just as that on the coil, acts as a sponge to entrap the metal oxide in contact with the wire, making for a more stable electrical connection. The whisker is cut to a length which would allow it to be inserted into the coil substantially parallel to an axis through the coil, while having enough material left extending outside of the coil to form an electrical lead once the semiconductor material has been applied. For best results, the metal whisker extends the length of the coil, and should be placed in the center of the coil. However, the whisker need not be placed in the center of the coil or substantially parallel to its axis in order for the sensor to work, in fact the whisker may touch the coil as long as an electrical short is not created between the coil and the whisker. Both the coil and the sensing wire should be annealed, such as by heating it to red heat, prior to coating the sensor with metal oxide. This will prevent the separation of the metal oxide from the coil or whisker when the sensor is initially or sequentially raised to its operating temperature.

A liquid solution containing the metal oxide semiconductor material which has been particularly chosen for its sensitivity to the object gas of interest, is then prepared. Both the preparation and the selection of these metal oxide semiconductor materials are well known to those skilled in the art. A number of those which are of particular interest are $WO_3$, $SnO_2$ and $NiO$. These oxides are useful in the detection of a variety of gases.

Other strong candidates for use as metal oxide detectors are those of the transition metals Sc, Ti, V, Cr, Mn, Fe, Co, Ni, Cu, Zn, Y, Zr, Nb, Mo, Tc, Ru, Rh, Pd, As, Cd, Hf, Ta, W, Re, Os, Ir and Pt as well as the Lanthanide series La, Ce, Pr, Nd, Pm, Sm, Eu, Gd, Tb, Dy, Ho, Er, Tm, Yb, and Lu or mixtures thereof. In addition, these elements are also considered good candidates as metal oxide components, Ge, Sn, Pb, As, Sb, Bi, Ga, In, and Tl.

These solutions can be made by dissolving the salt of the desired metal in a solvent, usually water. Although the concentration of the solution is not critical, it is preferred that the concentration be close to saturation in order to expedite the application of metal oxide onto the sensor. A solution which is too dilute will result in a greater number of applications of the solution to the sensor in order to build up the metal oxide to the required thickness, while too concentrated a solution will result in the metal salt precipitating out of solution.

In general, the metal oxide semiconductor solution may be placed onto the heater coil and whisker by any conventional means such as spraying, brushing or manually applying a small amount of liquid. After the semiconductor has been placed onto these components, it is dried by either passing an electrical current through the heater coil or by exposing it to an external heat source. In either case, the heating must be of sufficient duration and at a high enough temperature such that a constant output from the sensor whisker is attained when the semiconductive metal oxide is electrically self heated to near its operating temperature. This may be achieved when the temperature is high enough to convert the metal oxide semiconductor material to its active state, whereby it will respond properly when exposed to the object gas. It may be necessary to apply the metal oxide in a number of individual applications of the solution each of which is dried prior to the next application. During the preparation of these metal oxides, it is important that they remain porous so as to allow for the absorption of the gas of interest leading to greater sensitivity for these sensors. Common object gases which these sensors would be designed to detect include, but are not limited to $H_2S$, $CO$, $CO_2$, $CH_4$, $H_2$, etc.

Referring to FIG. 1, which depicts a detector 60 incorporating the current invention comprising a voltage source 40, a heater coil a sensing whisker 10, a biasing means 70 for adjusting the electrical potential difference between the heater and the whisker, a meter 50 for measuring the changes in the current flow to the whisker and the metal oxide material 30; operates as follows. A voltage 40 is applied to the heater coil 1 which heats the sensing unit to its proper operating temperature. At the same time, by the proper adjustment or selection of a biasing means 70, i.e. a resistor, the electrical potential difference between the coil and the sensing whisker is established. During this time, the detector 60 reaches a state of equilibrium with the semiconductor metal oxide 30 allowing a certain current to flow between the heater coil 1 and the sensor whisker 10. This current may be measured at the meter 50 and may be characterized as the baseline current. When the detector is subsequently exposed to a gas sample containing a gas to which the metal oxide semiconductor material is sensitive, its resistance will change causing an increase or decrease in the current flowing from the heater coil 1 to the whisker 10 which will change the current measurement at the meter 50.

There have been two surprising results stemming from gas sensors of the current design. The first surprising result is the low power consumption required in operating these sensors. As may be seen in the Example below, these sensors operate on less than 150 mW of power and typically about 60–100 mA at 1.2V which is about ½ the power requirement of the prior art sensors. The second surprising result is the fact that these sensors respond substantially linearly to the concentrations of the reactive gas to which they are exposed, at least over the concentrations of interest. This linearity of response allows for a greater sensitivity in detection of the reactive gas concentration over the most important concentrations. And, of course, the low power consumption makes these sensors much more attractive for use in portable gas sensing devices.

EXAMPLE

A tungsten oxide gas sensor for the detection of hydrogen sulfide gas was prepared as follows:

The heater element was formed using the green or uncured Secon Metals platinum/iridium ceramic coated filament wire described above. The wire was then wound on a 4 mil mandrel such that ten coils were wound in one direction and then ten more coils were wound in the reverse direction, FIG. 1. The coils for the second layer were ½ turn out of alignment to the initial coils, thereby giving a more compact arrangement. Each layer consisted of 10 coils. The coil was removed from the mandrel and the two leads, which come off at the same end of the coil, were shaped to form a "V" at approximately 10±5 degrees to the axis of the mandrel. Both leads were trimmed to allow ¼ inch extending from the point of exit from the coil.

The heater coil was then mounted on a base having four pins. The coil was spot welded to pin 1 and pin 4. The coil was electrically self-heated to red heat and allowed to return to room temperature to cure the alumina coating and render it porous. The cold resistance was tested and was found to be within the tolerances of about 9.30Ω to about 10.3 Ω.

The whisker sensor was then prepared by cutting a six-inch long piece of wire from the same Secon Metals wire used to form the heater coil. The whisker was then placed in a furnace and annealed by heating it to about 700° C for about ten minutes. The wire was then cut into ½ inch lengths. The whisker was then inserted through the coil lengthwise and one end of the whisker was spot welded to pin 2. The whisker was positioned substantially concentric with the axis of the heater coil. Excess wire was trimmed at the spot weld and the other end was trimmed to extend outside the coil to a length of about ⅛ that of the coil.

A metal oxide solution of ammonium tungstate in water whose concentration was close to saturation was applied directly to the coil and whisker as several applications using a pressurized hypodermic needle. The coating was then dried initially by applying approximately 0.55V across the coil for about thirty seconds. The dry metal oxide which was left on the coil and wire was then sintered by applying about 1.55V across the coil for about twenty seconds. No special atmosphere was required.

Figure 2:
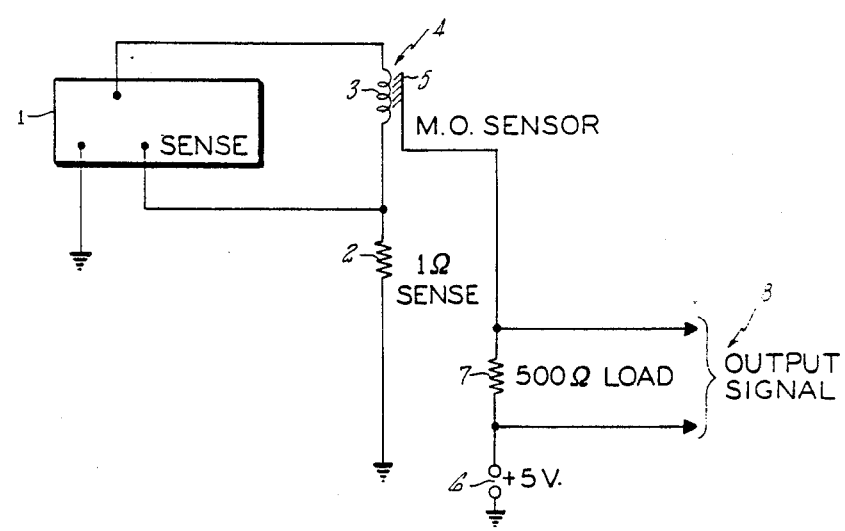
FIG. 2 depicts a typical electrical schematic for the present inventive gas detector.

The low power solid state semiconductor sensor constructed as above was tested in an atmosphere of about 0 to about 15 ppm of $H_2S$ in air. The test circuit in which this sensor was operated is depicted in FIG. 2. An electrical sensing unit 1 containing an electrical power source and an electrical sensing unit (not depicted) which in conjunction with the 1 ohm resistor 2 maintains a constant current flow through the coil 3 of the metal oxide gas sensor 4. A biasing current is maintained on the metal oxide sensing whisker 5 by having a 5V power source 6 and the 500 ohm resistor 7 in a series with it. The output signal 8, which is any change in the current flowing through the whisker due to the change in the resistance of the metal oxide, may be read on a meter (not shown). It should be pointed out that both FIG. 1 and FIG. 2 are meant to be exemplary and not limiting.

Although the circuit is depicted as being powered by a constant current source, it is not necessary as alternating current may also be used. The coil was powered with a DC voltage to produce about 95 mW of power. The results of this test are plotted in FIG. 3, the results having been normalized to 10 ppm.

Figure 3:
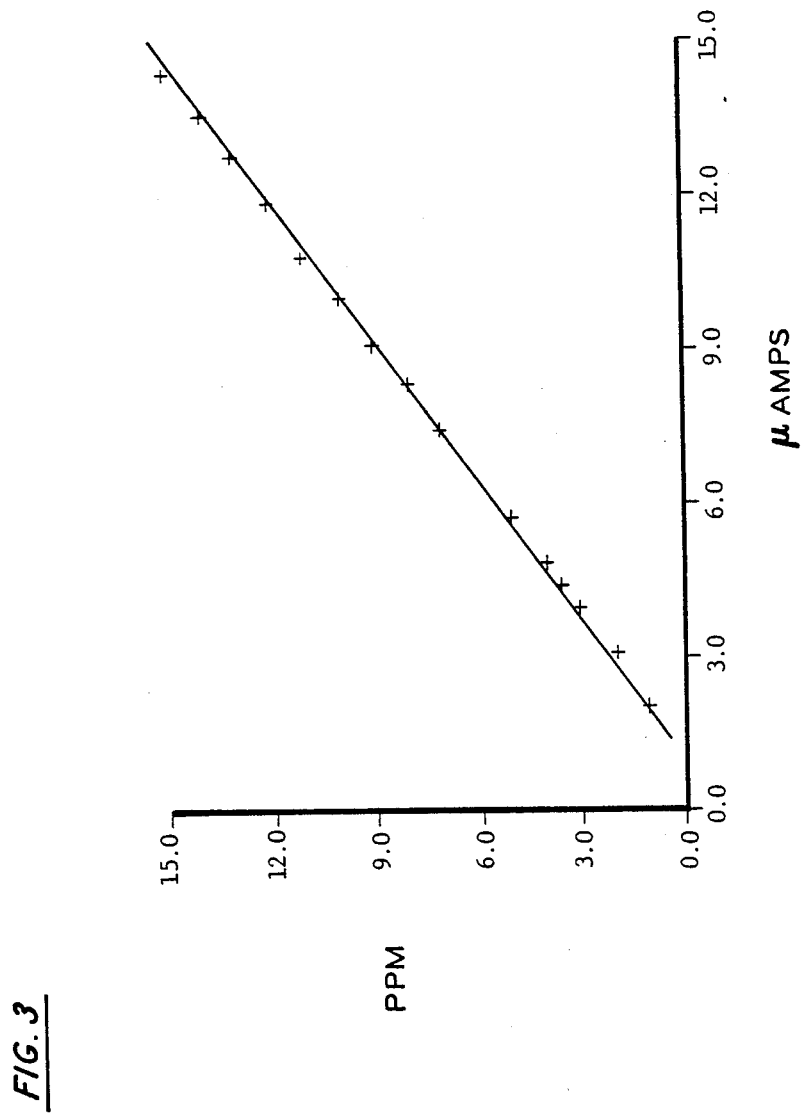
FIG. 3 is a graph of the response of a detector according to the present invention to different concentrations of $H_2S$ gas.

As may be seen from FIG. 3, the response of the detector is substantially linear in this range, although the response becomes less linear in higher ranges.

Generally these gas detectors comprise a means of introducing or drawing a gas sample into the detector, a means for exposing the sample gas to the gas sensor as well as a means for measuring the change in the resistance of the metal oxide. In addition, these units are generally battery powered. Gas detectors incorporating the present gas sensor will be useful in detecting dangerous gases such as $CO$, $CO_2$, $H_2S$, $H_2$, $Cl$ as well as combustible hydrocarbons, i.e. methane, propane, gasoline, etc.

Gas detectors incorporating the present sensor require far less energy to power them, as well as responding in a linear fashion over a significant concentration of the object gas, which make portable gas detecting units easier and cheaper to operate. One point which makes the unit easier to use is that due to its linear response, it need only be calibrated with a single calibration point. These units are cheaper to operate due to the low power consumption of the sensor requiring fewer battery charges and changes. The ease of operation coupled with the cost saving should allow more people to utilize these units to make their workplace safer.

It should be understood that the invention is not limited to the particular embodiments shown and described herein, but that various changes and modifications may be made without departing from the spirit and scope of this novel concept as defined by the following claims.

We claim:

1. A metal oxide semiconductor gas senor comprising a heating element formed in a continuous series of coils around a central axis from an electrically conductive wire coated with a porous electrically insulating layer, an electrically conductive sensing element positioned within but spaced from the electrically conductive wire in said heating element and substantially in a plane parallel to said central axis, and a porous metal oxide semiconductive material encapsulating said heating element and said sensing element; with said semiconductive material electrically contacting the conductive wire of said heating element through said porous electrically insulating layer.

2. The gas sensor of claim 1 wherein the coils of said heating element are tightly formed and the insulating layers of adjacent coils contact each other.

3. The gas sensor of claim 1 wherein the porous metal oxide is tungsten oxide.

4. The gas sensor of claim 1 wherein the metal oxide is selected from the group consisting of tungsten oxide, nickel oxide, stannous oxide, ferric oxide, molybdenum oxide, or mixtures thereof.

5. The gas sensor of claim 1 wherein the heating element is formed from $Al_2O_3$ insulated platinum-iridium wire.

6. The gas sensor of claim 1 wherein the sensing element is coated with a porous electrically insulating layer.

7. The gas sensor of claim 6 wherein the material of the insulating layer is a porous $Al_2O_3$.

8. A device for detecting the presence of an object gas, said device having an electrical power source, a gas sensor whose electrical conductivity changes with the concentration of the gas and a means for measuring this change in conductivity wherein said said sensor is the gas sensor of claim 1. c

* * * * *